United States Patent
Roach et al.

(10) Patent No.: US 8,123,793 B2
(45) Date of Patent: Feb. 28, 2012

(54) PRE-CRIMP BALLOON INFLATION

(75) Inventors: Tina Roach, Zimmerman, MN (US);
Eric Hallberg, Santiago, MN (US);
Tracy Buckman, Coon Rapids, MN
(US); Anthony Scales, Big Lake, MN
(US)

(73) Assignee: Boston Scientific Scimed, Inc.

( * ) Notice: Subject to any disclaimer, the term of this patent is extended or adjusted under 35 U.S.C. 154(b) by 676 days.

(21) Appl. No.: 12/207,743

(22) Filed: Sep. 10, 2008

(65) Prior Publication Data

US 2010/0063571 A1 Mar. 11, 2010

(51) Int. Cl.
*A61F 2/06* (2006.01)

(52) U.S. Cl. ....................... 623/1.11; 604/509

(58) Field of Classification Search .................. 604/509; 623/1.11, 1.12; 606/108; 29/515, 516
See application file for complete search history.

(56) References Cited

U.S. PATENT DOCUMENTS

| | | | |
|---|---|---|---|
| 5,015,231 A | 5/1991 | Keith et al. | |
| 5,292,331 A | 3/1994 | Boneau | |
| 5,445,646 A | 8/1995 | Euteneuer | |
| 5,836,965 A | 11/1998 | Jendersee et al. | |
| 5,976,181 A | 11/1999 | Whelan et al. | |
| 6,063,092 A | 5/2000 | Shin | |
| 6,159,229 A | 12/2000 | Jendersee et al. | |
| 6,187,013 B1 | 2/2001 | Stoltze | |
| 6,309,402 B1 | 10/2001 | Jendersee | |
| 6,823,576 B2 | 11/2004 | Austin | |
| 6,863,683 B2 * | 3/2005 | Schwager et al. | 623/1.11 |
| 6,942,681 B2 | 12/2005 | Johnson | |
| 6,986,785 B2 | 1/2006 | O'Shaughnessy | |
| 2003/0032999 A1 | 2/2003 | Huang | |
| 2005/0183259 A1 | 8/2005 | Eidenschink et al. | |
| 2005/0188525 A1 | 9/2005 | Weber et al. | |
| 2006/0074396 A1* | 4/2006 | Stiger | 604/509 |
| 2007/0067009 A1* | 3/2007 | Gandhi et al. | 623/1.11 |

FOREIGN PATENT DOCUMENTS

WO 95/33422 12/1995

* cited by examiner

*Primary Examiner* — Victor X Nguyen
(74) *Attorney, Agent, or Firm* — Seager Tufte & Wickhem LLC

(57) ABSTRACT

A method of crimping a stent onto a balloon of a stent delivery catheter is disclosed. The method includes pressurizing the balloon while the stent is being radially compressed onto the balloon with a crimping apparatus. Once the stent has reached its radially compressed configuration, the pressure within the balloon is released, while an inward crimping force exerted on the stent by the crimping apparatus is maintained. After a dwell time, the inward crimping force is discontinued, and the balloon and crimped stent are removed from the crimping apparatus. Resultant of the crimping process, balloon material extends radially outward through interstices of the stent to facilitate stent retention on the balloon while advancing the stent delivery catheter through a vessel lumen.

6 Claims, 6 Drawing Sheets

PRE-CRIMP BALLOON INFLATION

TECHNICAL FIELD

The disclosure is directed to securing a stent onto an inflation balloon of a stent delivery catheter. More particularly, the disclosure is directed to pressurizing an inflation balloon of a stent delivery catheter prior to crimping a stent onto the inflation balloon during a crimping process.

BACKGROUND

Medical devices such as stents, stent grafts, and vena cava filters are often utilized in combination with a delivery device for placement at a desired location within the body. A medical prosthesis such as a stent, for example, may be loaded onto a stent delivery device such as a balloon catheter and then introduced into the lumen of a body vessel in a configuration having a reduced diameter. Once delivered to a target location within the body, the stent may then be expanded to an enlarged configuration within the vessel to support and reinforce the vessel wall while maintaining the vessel in an open, unobstructed condition. In some medical procedures such as a percutaneous transluminal coronary angioplasty (PTCA), for example, the stent may be deployed and expanded within a vessel adjacent to the location where a lesion has been removed to prevent restenosis or prolapse of the vessel at that region. In some embodiments, the stent may be mechanically expanded by the inflation of a balloon on the delivery device.

Stents which are expandable by inflation of a balloon are typically secured to the balloon of a balloon catheter in a reduced diameter configuration or profile prior to their use. In some techniques, for example, the stents are loaded onto the balloon and then inserted into a crimping device which applies an inwardly directed radial force to the stent to reduce the diameter of the stent around the balloon.

In some techniques, for example as disclosed in U.S. Pat. No. 5,836,965 to Jendersee et al., the balloon material may be heated to an elevated temperature, such as greater than the glass transition temperature of the balloon material, causing the balloon material to soften and thus more easily conform to the contours of the stent. In other techniques, for example as disclosed in U.S. Pat. No. 5,976,181 to Whelan et al., the balloon material may be chemically treated in order to soften the balloon material such that the balloon material may more easily conform to the contours of the stent.

There is an ongoing desire to provide alternative methods and techniques to crimp a stent onto a stent delivery catheter. Furthermore, there is an ongoing desire to provide alternative arrangements of stent delivery systems.

SUMMARY

The disclosure is directed to several alternative designs, materials and methods of manufacturing medical device structures and assemblies.

Accordingly, one illustrative embodiment is a method of crimping a stent onto a balloon of a stent delivery catheter. The method includes loading a stent onto a balloon of a stent delivery catheter and positioning the stent and the balloon of the stent delivery catheter within a crimping apparatus. The balloon may then be pressurized to an inflation pressure in the range of about 0.4 atmospheres to about 4 atmospheres subsequent to loading the stent onto the balloon. While the balloon is pressurized to an inflation pressure in the range of about 0.4 atmospheres to about 4 atmospheres, a radially compressive force may be applied to the stent to crimp the stent onto the balloon. The pressure within the balloon may be released while the radially compressive force remains applied to the stent. At some time after the pressure is released from within the balloon the radially compressive force may be released from the stent.

Another illustrative embodiment is a method of crimping a stent onto a balloon of a stent delivery catheter. The method includes providing a crimping apparatus including a plurality of crimping elements forming a crimping lumen having a diameter, wherein the plurality of crimping elements are actuatable to alter the diameter of the crimping lumen. A stent loaded onto an inflation balloon of a stent delivery catheter may be positioned within the crimping lumen of the crimping apparatus. The inflation balloon may be inflated within the stent to a pressure of 4 atmospheres or less. The crimping elements may then be actuated radially inward toward the stent to apply a radially compressive crimping force to the stent while the inflation balloon is inflated, wherein balloon material is projected radially outward through interstices of a first end segment of the stent proximate a first end of the stent, and wherein balloon material is projected radially outward through interstices of a second end segment of the stent proximate a second end of the stent. The radially compressive crimping force may be maintained for a duration of time. The inflation balloon may be deflated while maintaining the radially compressive crimping force, wherein balloon material remains projected radially outward through the interstices of the first end segment of the stent proximate the first end of the stent after deflating the balloon, and wherein balloon material remains projected radially outward through the interstices of the second end segment of the stent proximate the second end of the stent after deflating the balloon. After the duration of time has lapsed, the crimping elements may be actuated radially outward away from the stent to discontinue the radially compressive crimping force, wherein balloon material remains projected radially outward through the interstices of the first end segment of the stent proximate the first end of the stent after discontinuing the radially compressive crimping force, and wherein balloon material remains projected radially outward through the interstices of the second end segment of the stent proximate the second end of the stent after discontinuing the radially compressive crimping force.

Another illustrative embodiment is a method of securing a stent onto a balloon of a stent delivery catheter. The method includes providing a stent loaded onto an inflation balloon of a stent delivery catheter. The stent includes a first longitudinal length of interconnected struts extending from the first end of the stent toward the second end of the stent. The interconnected struts of the first longitudinal length define interstices between adjacent interconnected struts of the first longitudinal length of interconnected struts. The stent also includes a second longitudinal length of interconnected struts extending from the second end of the stent toward the first end of the stent. The interconnected struts of the second longitudinal length define interstices between adjacent interconnected struts of the second longitudinal length of interconnected struts. The stent also includes a third longitudinal length of interconnected struts extending intermediate the first longitudinal length of interconnected struts and the second longitudinal length of interconnected struts. The interconnected struts of the third longitudinal length define interstices between adjacent interconnected struts of the third longitudinal length of interconnected struts. The stent, loaded onto the inflation balloon of the stent delivery catheter, may be positioned within a crimping apparatus. The inflation balloon may be pressurized within the stent and the stent may be crimped onto the inflation balloon while the inflation balloon is pressurized. At the conclusion of crimping the stent onto the balloon, balloon material of the balloon extends radially outward through the interstices of the first longitudinal length of interconnected struts from the inner peripheral surface toward the outer peripheral surface of the stent greater than half the thickness of the stent, and at the conclusion of crimping the stent onto the balloon, balloon material of the balloon extends radially outward through the interstices of the second longitudinal length of interconnected struts from the inner peripheral surface toward the outer peripheral surface of the stent greater than half the thickness of the stent. However, at the conclusion of crimping the stent onto the balloon, balloon material of the balloon does not extend radially outward through the interstices of the third longitudinal length of interconnected struts from the inner peripheral surface toward the outer peripheral surface of the stent greater than half the thickness of the stent. The stent and inflation balloon may then be removed from the crimping apparatus.

Another illustrative embodiment is a method of crimping a stent onto a balloon of a stent delivery catheter. The method includes loading a stent onto a balloon of a stent delivery catheter, and positioning the stent and the balloon of the stent delivery catheter within a crimping apparatus. The stent may then be crimped onto the balloon with the crimping apparatus. The balloon may be pressurized to an inflation pressure less than 6 atmospheres but greater than 0.4 atmospheres during the step of crimping the stent onto the balloon. After the step of pressuring the balloon, but while the stent and the balloon remain positioned within the crimping apparatus, the balloon may be depressurized. The stent and the balloon may then be removed from the crimping apparatus after the step of depressurizing the balloon.

Yet another illustrative embodiment is a stent delivery system including a stent delivery catheter including an elongate shaft and an inflation balloon secured to the elongate shaft. A stent is loaded onto the inflation balloon, wherein the stent has a first end, a second end and a length measured from the first end to the second end, and an outer peripheral surface, an inner peripheral surface and a thickness measured from the outer peripheral surface to the inner peripheral surface. The stent includes a first portion of interconnected struts located at the first end of the stent, the first portion of interconnected struts defining interstices between adjacent interconnected struts of the first portion of the stent; a second portion of interconnected struts located at the second end of the stent, the second portion of interconnected struts defining interstices between adjacent interconnected struts of the second portion of the stent; and a third portion of interconnected struts located intermediate the first portion and the second portion, the third portion of interconnected struts defining interstices between adjacent interconnected struts of the third portion of the stent. Balloon material of the balloon extends radially outward through the interstices of the first portion of the stent from the inner peripheral surface toward the outer peripheral surface of the stent greater than half the thickness of the stent, and balloon material of the balloon extends radially outward through the interstices of the second portion of the stent from the inner peripheral surface toward the outer peripheral surface of the stent greater than half the thickness of the stent. However, balloon material of the balloon does not extend radially outward through the interstices of the third portion of the stent from the inner peripheral surface toward the outer peripheral surface of the stent greater than half the thickness of the stent.

The above summary of some example embodiments is not intended to describe each disclosed embodiment or every implementation of the invention.

BRIEF DESCRIPTION OF THE DRAWINGS

The invention may be more completely understood in consideration of the following detailed description of various embodiments in connection with the accompanying drawings, in which.

Figure 1:
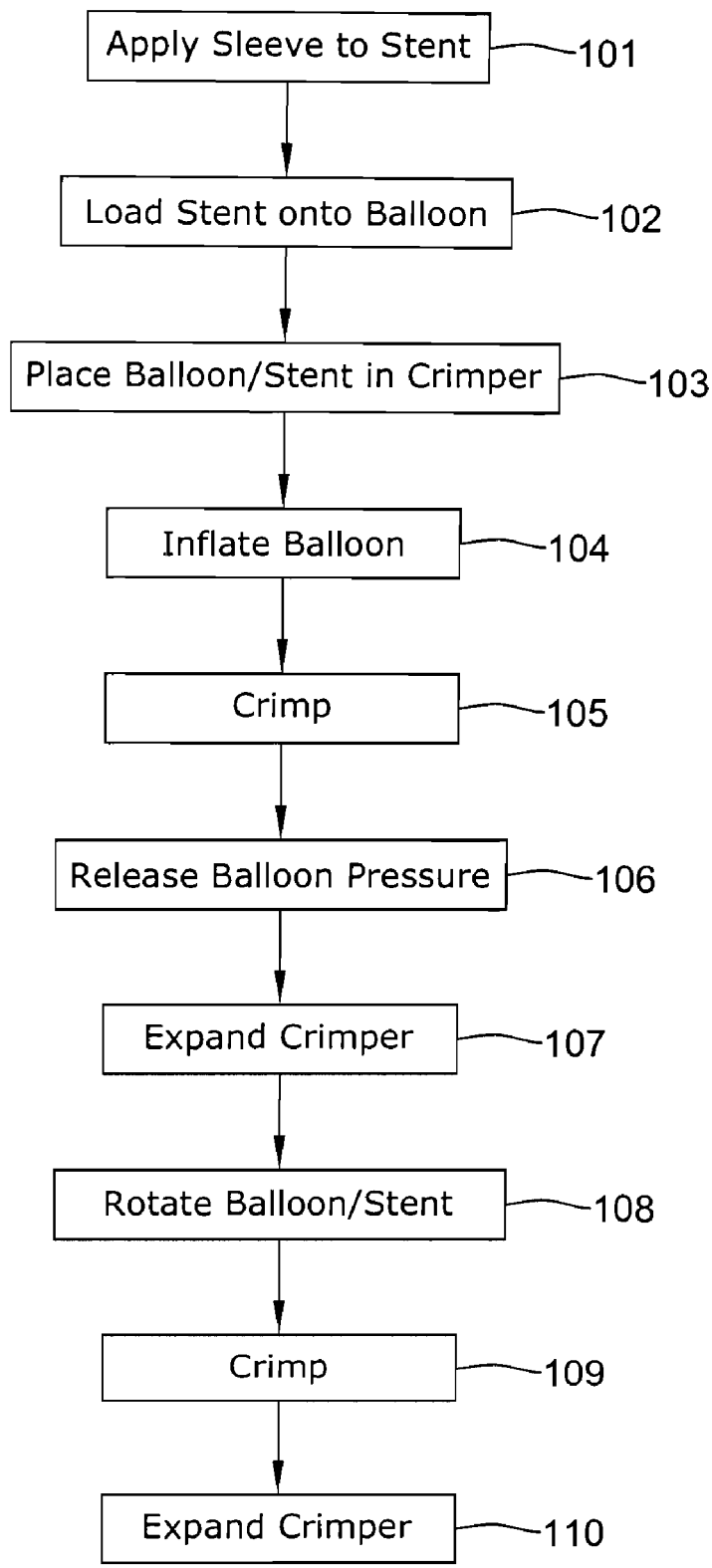
FIG. 1 is a schematic diagram of an illustrative stent crimping procedure for crimping a stent onto a balloon of a balloon catheter.

While the invention is amenable to various modifications and alternative forms, specifics thereof have been shown by way of example in the drawings and will be described in detail. It should be understood, however, that the intention is not to limit aspects of the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the invention. The illustrative embodiments depicted are intended only as exemplary. Selected features of any illustrative embodiment may be incorporated into an additional embodiment unless clearly stated to the contrary.

Referring now to FIG. 1, several steps involved in an exemplary stent crimping process are disclosed. During the stent crimping process, a stent may be compressed from a first, larger diameter pre-crimp configuration to a second, smaller diameter post-crimp configuration. Thus, prior to being crimped (e.g., radially compressed) the stent may be considered to have a pre-crimp configuration having a first diameter, and subsequent to being crimped the stent may be considered to have a post-crimp configuration having a second diameter less than the first diameter.

As indicated at Step 101 of FIG. 1, prior to being placed on the balloon of a stent delivery catheter, a crimping sleeve may be placed around the circumference of the stent. The crimping sleeve may help more uniformly distribute crimping forces around the stent during a stent crimping step and/or may help protect the stent and/or a coating on the stent during a stent crimping step. It is noted that in some embodiments the crimping sleeve may be placed on the stent after the stent has been loaded onto a balloon of a stent delivery catheter. In some embodiments, the step of placing a crimping sleeve onto the stent may be eliminated from the stent crimping process.

With the crimping sleeve positioned around the stent, the stent may be loaded onto a balloon of a stent delivery catheter, as indicated at Step 102. In some embodiments, the balloon of the stent delivery catheter may be folded around the elongate shaft of the stent delivery catheter prior to positioning the stent over the balloon. For example, in some embodiments, the balloon may be folded into a plurality of wings which are then folded around the circumference of the elongate shaft of the stent delivery catheter. In some embodiments, the stent may be positioned circumferentially around the balloon of the stent delivery catheter, and may be longitudinally centered between two radiopaque marker bands of the stent delivery catheter (which in some embodiments may be located interior of the balloon). As mentioned above, in some embodiments, a crimping sleeve may be positioned around the stent, prior to or after the stent has been loaded onto the balloon.

Next, as indicated at Step 103, the balloon of the stent delivery catheter and the stent may be positioned within a crimping apparatus. An exemplary crimping apparatus which may be used to crimp the stent onto the balloon may include a plurality of actuatable crimping blades disposed about a central crimping lumen. The actuatable crimping blades may be selectively actuated to increase the diameter of the central crimping lumen and/or decrease the diameter of the central crimping lumen. The crimping blades can be configured to move independently of each other or in unison, and can be configured to collectively contract inwardly towards the central axis of the crimping lumen and retract outwardly away from the central axis of the crimping lumen in order to adjust the size of the crimping lumen. Thus, the stent and the balloon of the stent delivery catheter may be positioned in the crimping lumen of the crimping apparatus with the crimping blades in a radially retracted or enlarged position. When contracted, each of the crimping blades can be configured to provide an inwardly directed radial force to the inserted stent assembly disposed in the crimping lumen in order to crimp the stent onto the balloon. Movement of the crimping blades can be accomplished using an actuation mechanism, which can include a number of levers, cams, bearings, connecting links, rods, cylinders, motors, gears, or the like. In use, the crimping apparatus may be used to reduce the diameter of a stent (e.g., crimp the stent) inserted within the crimping lumen onto the balloon of the stent delivery catheter. An illustrative crimping apparatus is described in U.S. Pat. No. 6,823,576, herein incorporated by reference in its entirety. However, it is noted that any other crimping apparatus for radially contracting a stent onto a balloon of a stent delivery catheter may be used, if desired.

As indicated at Step 104, prior to crimping the stent onto the balloon, the balloon may be inflated with an inflation fluid (e.g., air, saline, etc.). For instance, an inflation fluid may be advanced through a lumen of the elongate shaft of the stent delivery catheter, into the interior of the balloon to pressurize the balloon during the crimping process. It is noted that, as used herein, inflation of the balloon does not necessarily require that the balloon be fully inflated, but rather that the balloon be at least partially inflated with an inflation fluid, such that the inflation fluid is located within the interior of the balloon.

U.S. Pat. No. 6,863,683 to Schwager et al. describes a method of crimping a stent onto a balloon of a balloon catheter in which the balloon is pressurized to a pressure in the range of about 6 to 8 atmospheres (ATM) prior to crimping the stent onto the balloon. Thus, Schwager et el. Teaches pressurizing the balloon to a pressure greater than the nominal pressure necessary to deploy stent within a vessel. The pressure typically needed to deploy a stent within a vessel is 6 atmospheres or more. We have determined, however, that the crimping method taught throughout Schwager et al. may result in undesirable consequences of the stent delivery system. For instance, when a balloon is subjected to the pressures disclosed in Schwager et al., pressurization of the stent during the crimping process may lead to occurrences of the formation of pinhole perforations in the balloon material, resulting in potential failure of the balloon. Furthermore, we have determined that utilizing such pressures as disclosed in Schwager et al. during the crimping process may also cause the stent to undesirably lock onto the balloon, not allowing clean separation of the stent from the balloon during deployment of the stent during a medical procedure.

Dissimilarly, in the crimping process currently described, the interior of the balloon may be pressurized to a pressure of less than nominal pressure (i.e., less than 6 atmospheres) For example, the balloon may be pressurized to a pressure of about 5 psi to about 80 psi, about 10 psi to about 60 psi, about 20 psi to about 60 psi, or about 30 psi to about 60 psi. In some embodiments, the balloon may be inflated to a pressure less than 80 psi, less than 60 psi, less than 50 psi, less than 40 psi, less than 30 psi, less than 20 psi, less than 15 psi, or less than 10 psi, but greater than 5 psi. In some embodiments, the interior of the balloon may be pressurized to a pressure of about 0.4 Atmospheres (ATM) to about 5.5 ATM, about 0.4 ATM to about 4 ATM, about 1 ATM to about 4 ATM, or about 2 ATM to about 4 ATM. In some embodiments, the balloon may be inflated to a pressure less than 6 ATM, less than 5 ATM, less than 4 ATM, less than 3 ATM, less than 2 ATM, or less than 1 ATM, but greater than 0.4 ATM. We have found that utilizing these disclosed pressures in our crimping process, disadvantages associated with the crimping process described in Schwager et al. may be avoided.

With the balloon pressurized to a desired inflation pressure, the stent may be crimped onto the balloon of the stent delivery catheter, as indicated at Step 105. For example, while the balloon is pressurized, the crimping blades of the crimping apparatus may be actuated radially inward to reduce the diameter of the crimping lumen through which the stent and balloon are positioned. As the crimping blades are contracted radially inward, the crimping blades contact the stent (or crimping sleeve around the stent) and exert an inward crimping force on the stent to crimp the stent onto the balloon. The inward crimping force exerted on the stent causes the stent to radially contract around the balloon of the stent delivery catheter to a smaller diameter. As the inward crimping force increases, the stent may be continually contracted to a smaller diameter until a desired compressed diameter of the stent is attained. As the stent is radially contracted around the balloon, balloon material may be urged into interstices of the stent. When the inward crimping force reaches a desired magnitude (e.g., maximum inward crimping force), radial contraction of the crimping blades may be halted, leaving the crimping blades in a radially contracted position around the stent. The crimping blades, holding the stent in the radially contracted or crimped position at the maximum inward crimping force, may be maintained in the radially contracted position for a duration of time, called a dwell time. The inward crimping force exerted on the stent with the crimping blades in their radially contracted position may be maintained throughout the dwell time.

As the inward crimping force reaches the desired magnitude in which radial contraction of the crimping blades is halted, the pressure within the balloon may be released and/or reduced, as indicated at Step 106. In some embodiments, the pressure within the balloon may be released at the moment the inward crimping force reaches the desired magnitude (i.e., +/−0.5 seconds), the pressure within the balloon may be released just prior to when the inward crimping force reaches the desired magnitude (i.e., within 1 second), or the pressure within the balloon may be released just after the inward crimping force reaches the desired magnitude (i.e., within 1 second). Thus, in some embodiments the pressure within the balloon may be released within +/−1 second of the inward crimping force exerted on the stent reaching the desired maximum crimping force. In other embodiments, the pressure within the balloon may be released at another desired time during the crimping process. For example, in some embodiments, the pressure within the balloon may be released and/or reduced prior to crimping the stent onto the balloon of the stent delivery catheter, or the pressure within the balloon may be released and/or reduced while the stent is being radially contracted around the balloon of the stent delivery catheter. Thus, in some embodiments, the pressure within the balloon may be released and/or reduced prior to applying a radially inward crimping force to the stent, or the pressure within the balloon may be released and/or reduced while the crimping force exerted on the stent is being increased to and/or decreased from a maximum crimping force. When the balloon is depressurized, balloon material of the balloon is maintained within interstices of the stent defined by the interconnected struts.

With the pressure within the balloon released, the maximum inward crimping force may be maintained throughout the dwell time. For example, the maximum inward crimping force may be maintained for about 10 seconds, about 15 seconds, about 20 seconds, about 25 seconds, or about 30 seconds in some processes. In some embodiments the maximum inward crimping force may be exerted on the stent for a duration of time of 10 seconds or more, 15 seconds or more, 20 seconds or more, 25 seconds or more, or 30 seconds or more.

As indicated at Step 107, at the conclusion of the desired dwell time (i.e., the duration of time in which the maximum inward crimping force is maintained), the crimping blades of the crimping apparatus may be radially retracted outward away from the crimped stent. As the crimping blades are retracted radially outward and out of contact with the stent and/or crimping sleeve, the inward crimping force exerted on the stent is discontinued.

In some embodiments, as indicated at Step 108, once the crimping blades of the crimping apparatus are radially retracted outward after the initial crimping step 105, the stent and balloon may be rotated within the crimping lumen of the crimping apparatus prior to a subsequent or secondary crimping step 109. Rotation of the stent and balloon and crimping the stent in an additional crimping step may increase the uniformity of the crimped stent around the balloon. In some embodiments, the stent and balloon may be rotated about 5 degrees, about 10 degrees, about 15 degrees, about 20 degrees, about 30 degrees, about 60 degrees, about 90 degrees, about 120 degrees about 180 degrees between the primary crimping step (i.e., the first crimping step 105) and the secondary crimping step (i.e., the second crimping step 109). If a crimping sleeve (positioned over the stent at step 101) is used during the crimping process, the crimping sleeve may remain on the stent during the secondary crimping step 109.

During the secondary crimping step, as indicated at Step 109, the crimping blades of the crimping apparatus may again be radially contracted inward in contact with the stent (or the crimping sleeve surrounding the stent) to apply an inward crimping force to the stent positioned around the balloon. During the secondary crimping step, the crimping blades may be actuated radially inward such that the crimping lumen is reduced to the same diameter that was maintained throughout the dwell time of the primary crimping step 105, to a diameter greater than the diameter that was maintained throughout the dwell time of the primary crimping step 105, or to a diameter less than the diameter that was maintained throughout the dwell time of the primary crimping step 105. During the secondary crimping step indicated at Step 109, the balloon may not be pressurized, and/or a vacuum may be applied to the interior of the balloon to evacuate fluid from the balloon.

After the secondary crimping step 109, the crimping blades of the crimping apparatus may be radially retracted outward to expand the crimping lumen, as indicated at Step 110. Once the crimping blades are radially retracted outward away from the stent, the balloon of the stent delivery catheter with the crimped stent disposed thereon, may be removed from the crimping apparatus. If a crimping sleeve was used during the crimping process, the crimping sleeve may then be removed from the stent and balloon.

In other embodiments, the secondary crimping stent may be eliminated. In such embodiments, once the crimping blades are radially retracted outward away from the stent as indicated at Step 107, the balloon of the stent delivery catheter with the crimped stent disposed thereon may be removed from the crimping apparatus. Thus, Steps 108, 109 and 110 indicated in FIG. 1 may be eliminated during some crimping processes.

Throughout the crimping process, the balloon may not be thermally heated or subjected to a chemical modification. In other words, during the crimping process, the molecular stability of the balloon material may be unmodified. The crimping process may be carried out at a substantially constant temperature, such as an ambient room temperature of about 18-22° C. Thus, the balloon material may remain at a substantially constant temperature, such as a temperature of about 18-22° C., prior to the crimping process, throughout the crimping process, and following to the crimping process. Furthermore, the molecular structure of the balloon material may remain chemically unmodified prior to the crimping process, throughout the crimping process, and following the crimping process. In other embodiments, throughout the crimping process or during a portion of the crimping process, the balloon may be thermally heated or subjected to a chemical modification, if desired.

Figure 2:
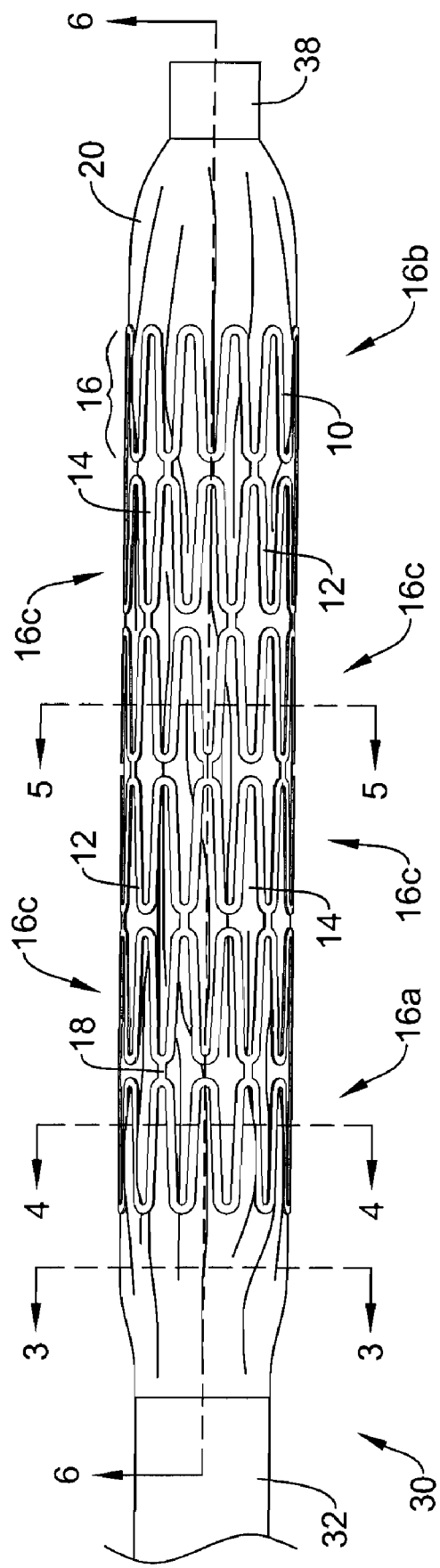
FIG. 2 is a side view of a distal portion of a balloon catheter including a stent crimped onto the balloon of the balloon catheter according to the stent crimping procedure described in FIG. 1.

FIG. 2 is a plan view of a stent 10 crimped onto the balloon 20 of a stent delivery catheter 30 resultant of the crimping process illustrated in FIG. 1. The balloon 20 may be secured to the elongate shaft of the stent delivery catheter 30. For instance, as further illustrated in FIG. 6, a proximal waist 22 of the balloon 20 may be secured (e.g., adhesively or thermally bonded) to an outer tubular member 32 of the elongate shaft of the stent delivery catheter 30, and a distal waist 24 of the balloon 20 may be secured (e.g., adhesively or thermally bonded) to an inner tubular member 34 of the elongate shaft of the stent delivery catheter 30. The stent delivery catheter 30 may include a distal tip 38, such as an atraumatic tip, at the distal end of the stent delivery catheter 30.

Figure 6:
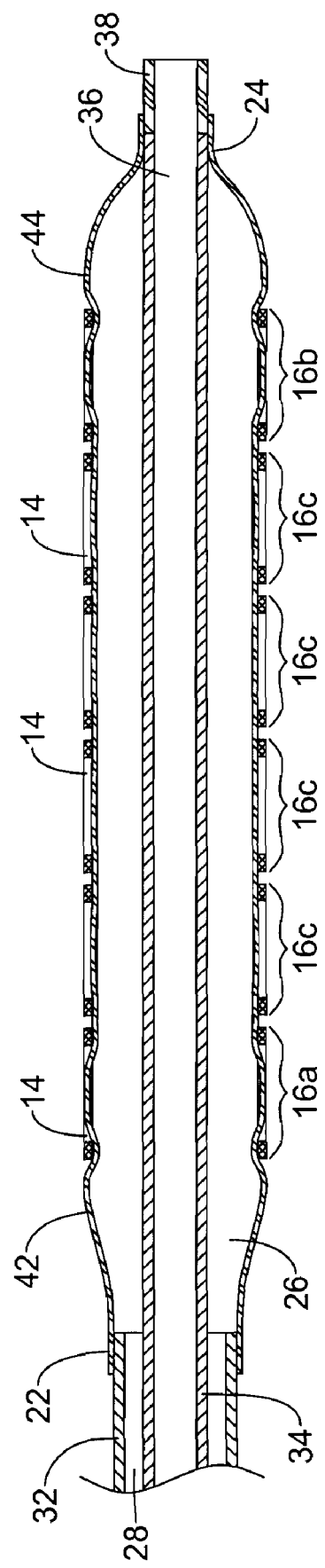
FIG. 6 is a cross-sectional view parallel to the longitudinal axis of the balloon catheter taken along line 6-6 of FIG. 2.

Furthermore, as shown in FIG. 6, the inner tubular member 34 may define a guidewire lumen 36 through which a guidewire may be positioned during a medical procedure. The guidewire lumen 36 may extend from the distal end of the stent delivery catheter 30 to a hub assembly located at the proximal end of the stent delivery catheter 30, or the guidewire lumen 36 may extend from the distal end of the stent delivery catheter 30 to an exit port located distal of the proximal end of the stent delivery catheter 30. Thus, the stent delivery catheter 30 may be guided over a guidewire as the stent delivery catheter 30 is advanced through a vessel lumen. Additionally, the interior 26 of the balloon 20 may be in fluid communication with an inflation lumen 28 of the stent delivery catheter 30. As shown in FIG. 6, in some embodiments the inflation lumen 28 may be defined by the space, such as an annular space, between the inner surface of the outer tubular member 32 and the outer surface of the inner tubular member 34.

The stent 10 includes a plurality of interconnected struts 12 defining interstices 14 between adjacent struts 12. As shown in FIG. 2, in some embodiments, the stent 10 may include a plurality of segments 16 of interconnected struts 12 longitudinally spaced along the length of the stent 10. For instance, each of the plurality of segments 16 may include a plurality of expandable interconnected struts 12 extending circumferentially around the circumference of the stent 10 in a serpentine pathway. Each of the plurality of segments 16 may be connected to an adjacent segment 16 of the stent 10 via a plurality of links 18 bridging between adjacent segments 16. For example, the stent 10 may include a first end segment 16a, or proximal segment, located at the proximal end of the stent 10; a second end segment 16b, or distal segment, located at the distal end of the stent 10; and one or more intermediate or medial segments 16c located intermediate of the first end segment 16a and the second end segment 16b. The stent 10 illustrated in FIG. 2 includes four intermediate segments 16c, however, it can be appreciated that the stent 10 may include one, two, three, four, five, six, seven, eight, or more intermediate segments 16c between the most proximal segment 16a and the most distal segment 16b of the stent 10. In some embodiments, each segment 16 of the stent 10 may have a length of about 1 millimeter. In other words, in some embodiments, the length of each of the segments 16 of the stent 10, measured in the longitudinal direction parallel to the longitudinal central axis of the stent 10, may be about 1 millimeter.

At the conclusion of the crimping process described herein, balloon material of the balloon 20 may extend into the interstices 14 of a first portion of interconnected struts 12 of the stent 10 located at the first end of the stent 10, and balloon material of the balloon 20 may extend into the interstices 14 of a second portion of interconnected struts 12 of the stent 10 located at the second end of the stent 10.

In some embodiments, the stent 10 may include a first portion of interconnected struts 12 located at the first end of the stent 10, a second portion of interconnected struts 12 located at the second end of the stent 10, and a third portion of interconnected struts 12 located intermediate the first portion and the second portion. At the conclusion of the disclosed crimping process, balloon material of the balloon 20 may extend radially outward within the interstices 14 of the first portion of the stent 10 proximate the first end of the stent 10, and balloon material of the balloon 20 may extend radially outward within the interstices 14 of the second portion of the stent 10 proximate the second end of the stent 10. The balloon material may extend outward within the interstices 14 of the first and second portions of the stent 10 greater than half the radial thickness of the stent 10. Furthermore, at the conclusion of the crimping process, balloon material may not appreciably extend radially outward within the interstices 14 of the third portion of the stent 10. In some embodiments, balloon material may extend outward within the interstices of the third portion of the stent 10 less than half the radial thickness of the stent 10. In some embodiments, at the conclusion of the crimping process, balloon material may not be located within interstices 14 of the stent 10 throughout the third portion of the stent 10.

In some embodiments, the first portion of the stent 10 may include at least the first end segment 16a of interconnected struts 12 of the stent 10, and the second portion of the stent 10 may include at least the second end segment 16b of interconnected struts 12 of the stent 10. In some embodiments, the third portion of the stent 10 may include at least a portion of the one or more intermediate segments 16c of interconnected struts 12 of the stent 10. In some embodiments, the third portion of the stent 10 may include the entirety of the one or more intermediate segments 16c. However, in some embodiments, the first portion of the stent 10 may include at least a portion of the one or more intermediate segments 16c and/or the second portion of the stent 10 may include at least a portion of the one or more intermediate segments 16c.

In some embodiments, the stent 10 may have a length of 4 millimeters or more. At the conclusion of the disclosed crimping process, balloon material may be located within interstices 14 of the stent 10 throughout a proximalmost 1 millimeter of the length of the stent 10, and/or balloon material may be located within interstices 14 of the stent 10 throughout a distalmost 1 millimeter of the length of the stent 10. Furthermore, in some embodiments, balloon material may not be located within interstices 14 of the stent 10 throughout an intermediate portion of the length of the stent 10.

The stent 10 may include a first longitudinal length of interconnected struts 12 extending from the first end of the stent 10 toward the second end of the stent 10, a second longitudinal length of interconnected struts 12 extending from the second end of the stent 10 toward the first end of the stent 10, and a third longitudinal length of interconnected struts 12 extending intermediate the first longitudinal length of interconnected struts 12 and the second longitudinal length of interconnected struts 12. In some embodiments, the first longitudinal length, the second longitudinal length, and the third longitudinal length may together represent the entire longitudinal length of the stent 10.

During the crimping process, balloon material may be induced radially outward through the interstices 14 of the first longitudinal length of interconnected struts 12 from the inner peripheral surface of the stent 10 toward the outer peripheral surface of the stent 10, and balloon material may be induced radially outward through the interstices 14 of the second longitudinal length of interconnected struts 12 from the inner peripheral surface of the stent 10 toward the outer peripheral surface of the stent 10. In some embodiments, balloon material may be induced radially outward through the interstices 14 of the first longitudinal length and the second longitudinal length greater than half the radial thickness of the stent 10. At the conclusion of the crimping process, balloon material may not extend radially outward through the interstices 14 of the third longitudinal length of the stent 10 greater than half the radial thickness of the stent 10.

As will be discussed further herein, it can be seen in FIG. 2 that at the conclusion of the described crimping process, balloon material of the balloon 20 may extend into the interstices 14 of the first end segment 16a and the second end segment 16b. The balloon material of the balloon 20 may help retain the stent 10 on the balloon 20 of the balloon catheter 30 prior to deployment within a vessel lumen. Thus, the balloon material located in the interstices 14 of the stent 10 may inhibit the stent 10 from sliding either proximally or distally relative to the balloon 20 during insertion of the balloon catheter 30 within a vessel lumen.

As can be seen in FIG. 2, the first end segment 16a includes interstices 14 which are open at the proximal end of the stent 10. In other words, the first end segment 16a includes interstices 14 which extend from the proximal end of the stent 10 distally, wherein the interstices 14 are longitudinally accessible from the proximal end of the stent 10. Furthermore, the second end segment 16b includes interstices 14 which are open at the distal end of the stent 10. In other words, the second end segment 16b includes interstices 14 which extend from the distal end of the stent 10 proximally, wherein the interstices 14 are longitudinally accessible from the distal end of the stent 10.

Resultant of the disclosed crimping process, balloon material from the balloon may extend into the interstices 14 which are open at the proximal end of the stent 10 and/or balloon material from the balloon may extend into the interstices 14 which are open at the distal end of the stent 10. In other words, at the conclusion of the crimping process, balloon material may extend radially outward from the inner surface of the stent 10 toward the outer surface of the stent 10 through the interstices 14 of the first end segment 16a and/or balloon material may extend radially outward from the inner surface of the stent 10 toward the outer surface of the stent 10 through the interstices 14 of the second end segment 16b.

Thus, at the conclusion of the described crimping process, balloon material may be located within the interstices 14 of the first end segment 16a throughout a proximalmost 1 millimeter of the length of the stent 10, and balloon material may be located within the interstices 14 of the second end segment 16b through a distalmost 1 millimeter of the length of the stent 10.

Figure 3:
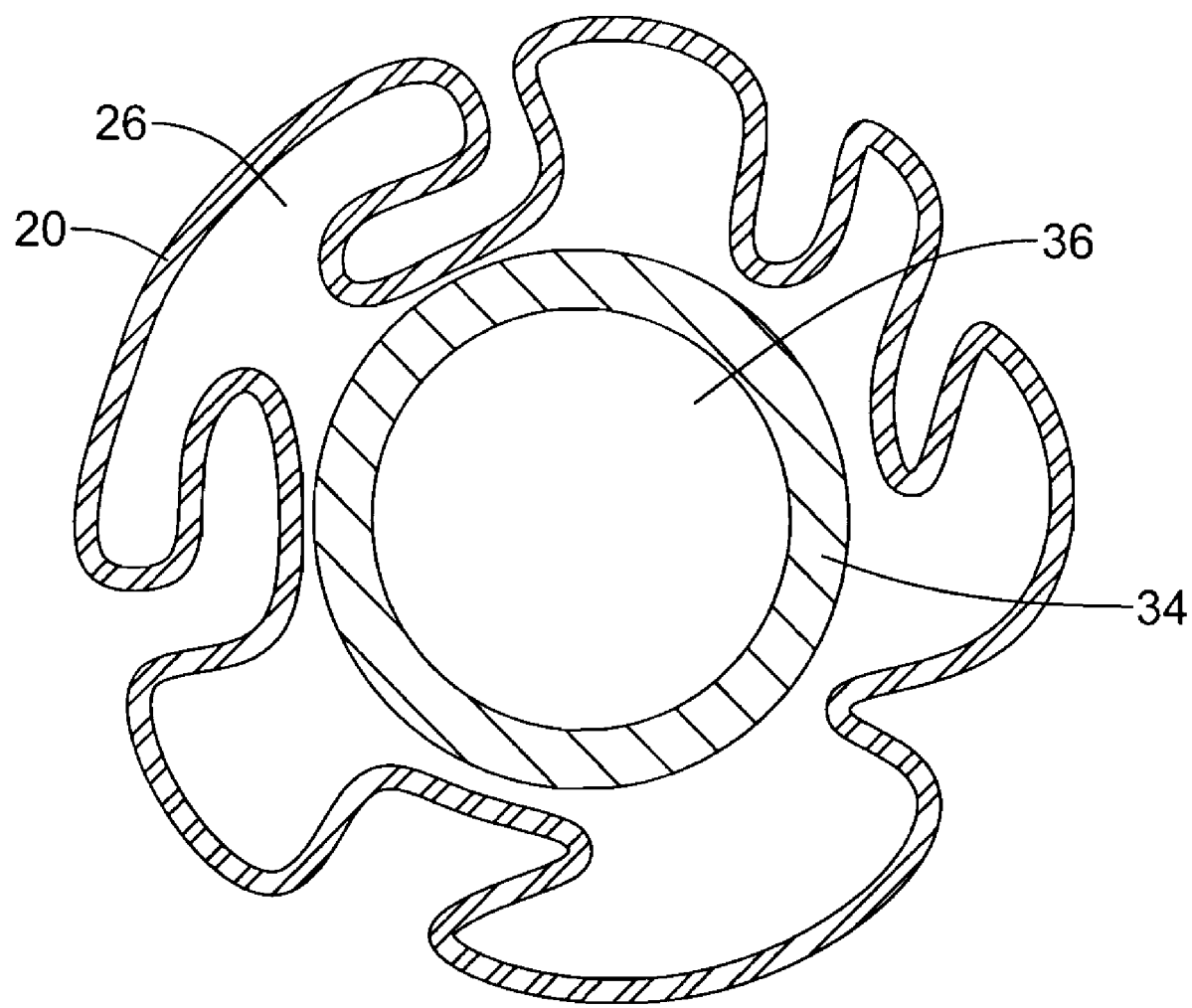
FIG. 3 is a cross-sectional view transverse to the longitudinal axis of the balloon catheter taken along line 3-3 of FIG. 2.

FIG. 3 is a transverse cross-sectional view of the stent delivery catheter 30 shown in FIG. 2 taken along line 3-3. The cross-section shown in FIG. 3 is taken through the proximal cone portion of the balloon 20. As can be seen from FIG. 3, the balloon 20 may be irregularly folded around the inner tubular member 34 of the stent delivery catheter 30 at locations proximal of the proximal end of the stent 10. Similarly, the balloon 20 may be irregularly folded around the inner tubular member 34 of the stent delivery catheter 30 at locations distal of the distal end of the stent 10.

Figure 4:
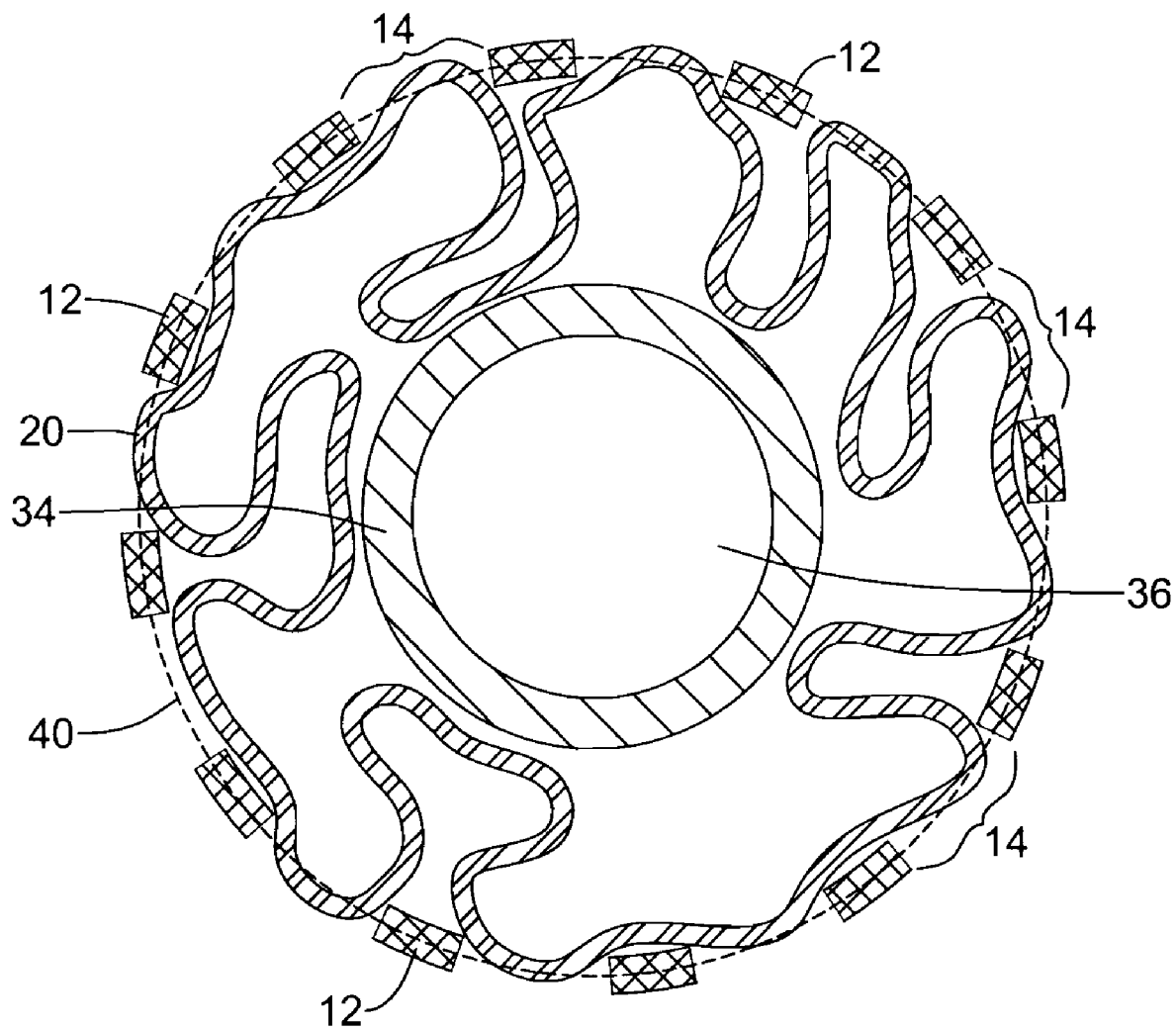
FIG. 4 is a cross-sectional view transverse to the longitudinal axis of the balloon catheter taken along line 4-4 of FIG. 2.

FIG. 4 is a transverse cross-sectional view of the stent delivery catheter 30 shown in FIG. 2 taken along line 4-4. The cross-section shown in FIG. 4 is taken through the first end segment 16a of the stent 10. It is noted that the cross-section shown in FIG. 4 may also be illustrative of a cross-section taken through the second end segment 16b of the stent 10.

Included in FIG. 4 is a dashed line 40 representing the radial midpoint between the inner peripheral surface of the stent 10 and the outer peripheral surface of the stent 10. In other words, the interconnected struts 12 of the stent 10 may have a thickness measured radially from the inner peripheral surface of the stent 10 to the outer peripheral surface of the stent 10. The dashed line 40 shown in FIG. 4 is located at the location representing one-half of the radial thickness of the interconnected struts 12 of the stent 10.

As shown in FIG. 4, at the conclusion of the described crimping process, balloon material of the balloon 20 extends radially outward through the interstices 14 of the first end segment 16a of the stent 10 from the inner surface of the stent 10 toward the outer surface of the stent 10. Likewise, at the conclusion of the described crimping process, balloon material of the balloon 20 extends radially outward through the interstices 14 of the second end segment 16b of the stent 10 from the inner surface of the stent 10 toward the outer surface of the stent 10. Within the first end segment 16a and the second end segment 16b, balloon material of the balloon 20 may extend radially outward through the interstices 14 of the stent 10 greater than half the thickness of the stent 10. In some embodiments, within the first end segment 16a and the second end segment 16b, balloon material of the balloon 20 may extend radially outward through the interstices 14 of the stent 10 more than 50%, more than 60%, more than 70%, more than 80%, or more than 90% of the radial thickness of the interconnected struts 12 of the stent 10.

As shown in FIG. 4, the configuration of the stent 10 provides a plurality of interstices 14 around the circumference of the stent 10. At the conclusion of the crimping process, balloon material of the balloon 20 may or may not extend radially outward through each of the interstices 14 of the first end segment 16a of the stent 10 greater than half the thickness of the stent 10. For instance in some embodiments, at the conclusion of the crimping process, balloon material of the balloon 20 may extend radially outward through a majority of the interstices 14 of the first end segment 16a of the stent 10 greater than half the thickness of the stent 10. In some embodiments, balloon material may extend radially outward through 10% or more, 20% or more, 30% or more, 40% or more, 50% or more, 60% or more, 70% or more, 80% or more, or 90% or more of the interstices 14 of the first end segment 16a of the stent 10.

Likewise, at the conclusion of the crimping process, balloon material of the balloon 20 may or may not extend radially outward through each of the interstices 14 of the second end segment 16b of the stent 10 greater than half the thickness of the stent 10. For instance in some embodiments, at the conclusion of the crimping process, balloon material of the balloon 20 may extend radially outward through a majority of the interstices 14 of the second end segment 16b of the stent 10 greater than half the thickness of the stent 10. In some embodiments, balloon material may extend radially outward through 10% or more, 20% or more, 30% or more, 40% or more, 50% or more, 60% or more, 70% or more, 80% or more, or 90% or more of the interstices 14 of the second end segment 16b of the stent 10.

Figure 5:
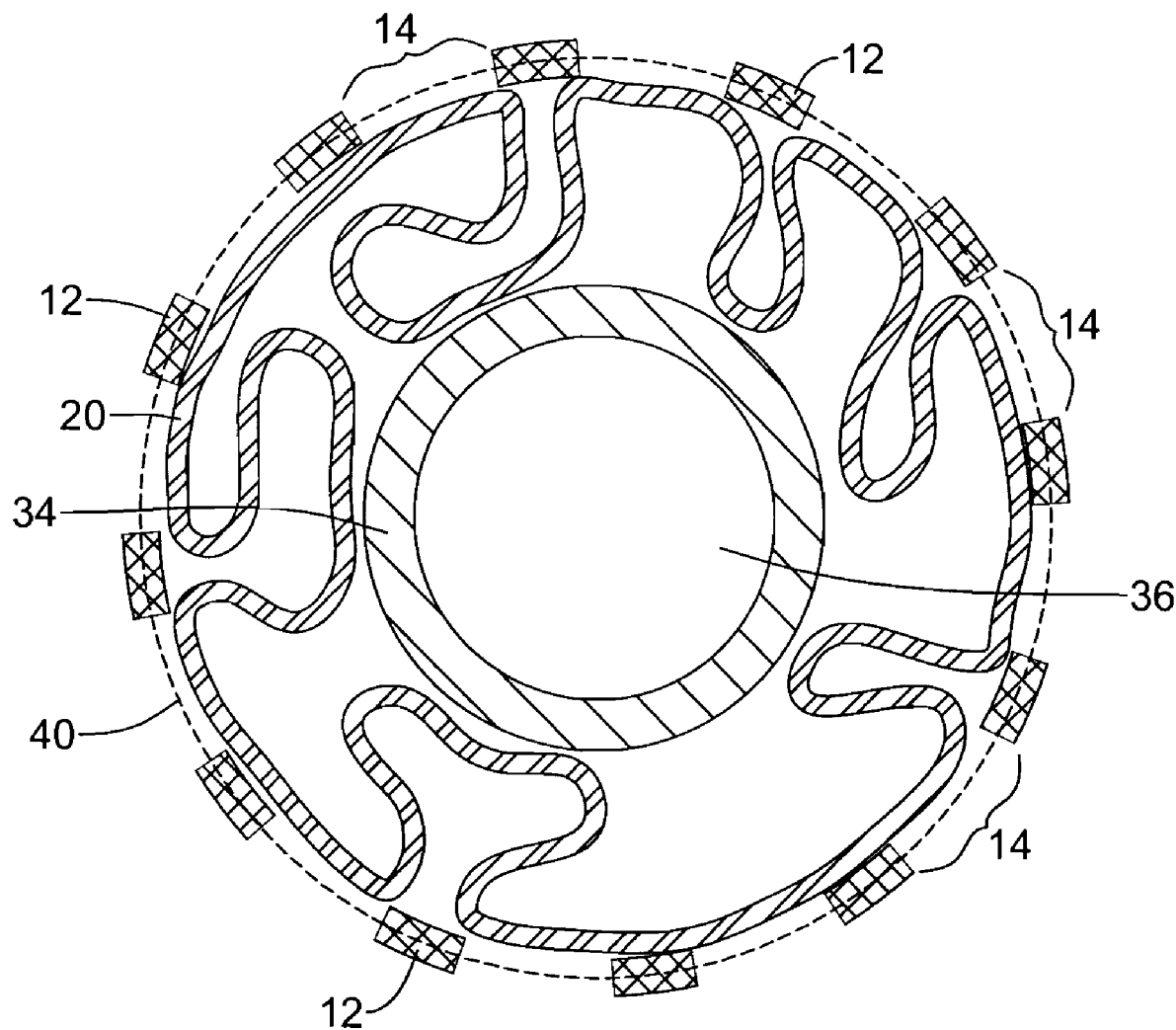
FIG. 5 is a cross-sectional view transverse to the longitudinal axis of the balloon catheter taken along line 5-5 of FIG. 2.

FIG. 5 is a transverse cross-sectional view of the stent delivery catheter 30 shown in FIG. 2 taken along line 5-5. The cross-section shown in FIG. 5 is taken through one of the plurality of intermediate segments 16c of the stent 10. It is noted that the cross-section shown in FIG. 5 may also be illustrative of a cross-section taken through one of the other intermediate segments 16c of the stent 10. The dashed line 40 representing the radial midpoint between the inner peripheral surface of the stent 10 and the outer peripheral surface of the stent 10 is also illustrated in FIG. 5.

As shown in FIG. 5, at the conclusion of the described crimping process, balloon material of the balloon 20 may not appreciably extend radially outward through the interstices 14 of the intermediate segments 16c of the stent 10 from the inner surface of the stent 10 toward the outer surface of the stent 10. Throughout the intermediate segments 16c, balloon material of the balloon 20 may extend radially outward through the interstices 14 of the stent 10 less than half the thickness of the stent 10. In some embodiments, throughout the intermediate segments 16c, balloon material of the balloon 20 may extend radially outward through the interstices 14 of the stent 10 less than 50%, less than 40%, less than 30%, less than 20%, or less than 10% of the radial thickness of the interconnected struts 12 of the stent 10. Thus, balloon material of the balloon 20 may not extend radially outward through the interstices 14 of the intermediate segments 16c of the stent 10 greater than half the radial thickness of the interconnected struts 12 of the stent 10 at the conclusion of the crimping process.

FIG. 6 further illustrates the interaction of the balloon material of the balloon 20 and the stent 10 at the conclusion of the described crimping process. As shown in FIG. 6, balloon material of the balloon 20 noticeably extends radially outward through interstices 14 of the first end segment 16a and the second end segment 16b, but balloon material of the balloon 20 does not appreciably extend radially outward through the interstices 14 of the intermediate segments 16c of the stent 10. Thus, throughout a central longitudinal portion of the stent 10 the balloon material of the balloon 20 does not extend radially outward through the interstices 14 of the stent 10 more than half the radial thickness of the interconnected struts 12 of the stent 10. Whereas, throughout the end portions of the stent 10 the balloon material of the balloon 20 does extend radially outward through the interstices 14 of the stent 10 more than half the radial thickness of the interconnected struts 12 of the stent 10.

Furthermore, as shown in FIG. 6, in some embodiments at the conclusion of the crimping process, the balloon 20 may include a proximal pillow 42 of balloon material proximal of the proximal end of the stent 10 and a distal pillow 44 of balloon material distal of the distal end of the stent 10. The proximal pillow 42 of balloon material may have an outer diameter greater than the inner diameter of the stent 10, and the distal pillow 44 of balloon material may have an outer diameter greater than the inner diameter of the stent 10. The proximal pillow 42 and/or the distal pillow 44 may be formed during the crimping process as the stent 10 is compressed radially inward onto the pressurized balloon 20. As the pressurized balloon 20 is being pushed radially inward by the stent 10 as the stent is being crimped onto the balloon 20, the portions of the balloon 20 proximal of and distal of the stent 10 tend to puff out as the fluid within the balloon 20 is displaced. The proximal pillow 42 and/or the distal pillow 44 may help secure the stent 10 onto the balloon 20. For instance, the proximal pillow 42 may inhibit the stent 10 from inadvertently sliding proximally on the balloon 20, preventing premature dislodgement of the stent 10 from the balloon 20 while delivering the stent 10 through the vasculature of a patient during a medical procedure. Furthermore, the distal pillow 44 may inhibit the stent 10 from inadvertently sliding distally on the balloon 20, preventing premature dislodgement of the stent 10 from the balloon 20 while delivering the stent 10 through the vasculature of a patient during a medical procedure.

The disclosed crimping process and resultant stent delivery system securely retains a stent onto a balloon of a balloon catheter to prevent premature dislodgement of the stent from the balloon while delivering the stent through the vasculature of a patient during a medical procedure, yet allows dissociation or separation of the stent from the balloon during deployment of the stent at a target location within the vasculature of a patient.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. A method of crimping a stent onto a balloon of a stent delivery catheter, the method comprising:
   providing a crimping apparatus;
   loading a stent onto a balloon of a stent delivery catheter; wherein the stent includes:
      a first portion of interconnected struts located at a first end of the stent, the first portion of interconnected struts defining interstices between adjacent interconnected struts of the first portion;
      a second portion of interconnected struts located at a second end of the stent, the second portion of interconnected struts defining interstices between adjacent interconnected struts of the second portion; and
      a third portion of interconnected struts located intermediate the first portion and the second portion, the third portion of interconnected struts defining interstices between adjacent interconnected struts of the third portion;
   positioning the stent and the balloon of the stent delivery catheter within the crimping apparatus;
   pressurizing the balloon to an inflation pressure in the range of about 0.4 atmospheres to about 4 atmospheres subsequent to loading the stent onto the balloon;
   applying a radially compressive force to the stent to crimp the stent onto the balloon while the balloon is pressurized to an inflation pressure in the range of about 0.4 atmospheres to about 4 atmospheres;
   releasing the pressure within the balloon while the radially compressive force remains applied to the stent; and
   releasing the radially compressive force from the stent after the pressure is released from within the balloon;
   wherein upon conclusion of the crimping process balloon material extends radially outward within the interstices of the first portion of the stent proximate the first end of the stent, and wherein balloon material extends radially outward within the interstices of the second portion of the stent proximate the second end of the stent.

2. The method of claim 1, wherein upon conclusion of the crimping process balloon material does not appreciably extend radially outward within the interstices of the third portion of the stent.

3. The method of claim 2, wherein the stent includes a first end segment of interconnected struts located proximate the first end of the stent, a second end segment of interconnected struts located proximate the second end of the stent, and one or more intermediate segments of interconnected struts located intermediate the first end segment and the second end segment;

wherein the first portion of the stent includes at least the first end segment of interconnected struts;

wherein the second portion of the stent includes at least the second end segment of interconnected struts; and wherein the third portion of the stent includes at least a portion of the one or more intermediate segments of interconnected struts.

4. The method of claim 3, wherein the first portion of the stent includes at least a portion of the one or more intermediate segments of interconnected struts.

5. The method of claim 4, wherein the second portion of the stent includes at least a portion of the one or more intermediate segments of interconnected struts.

6. The method of claim 1, further comprising the following steps after releasing the radially compressive force from the stent after the pressure is released from within the balloon:

rotating the stent and balloon within the crimping apparatus;

applying a radially compressive force to the stent after the step of rotating the stent and balloon within the crimping apparatus; and releasing the radially compressive force.

* * * * *